US006645252B2

(12) United States Patent
Asai et al.

(10) Patent No.: US 6,645,252 B2
(45) Date of Patent: Nov. 11, 2003

(54) DRIVE UNIT FOR PROSTHETIC LIMB

(75) Inventors: Masahiro Asai, Saitama (JP); Masaki Ban, Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/055,354

(22) Filed: Jan. 25, 2002

(65) Prior Publication Data

US 2002/0103543 A1 Aug. 1, 2002

(30) Foreign Application Priority Data

Jan. 26, 2001 (JP) .................................... 2001-019120

(51) Int. Cl.[7] .............................. A61F 2/70; A61F 2/74
(52) U.S. Cl. ............................................. 623/24; 623/26
(58) Field of Search .............................. 623/24, 26, 39, 623/40

(56) References Cited

FOREIGN PATENT DOCUMENTS

| SU | 191054 | * | 1/1967 | ................... 623/25 |
| SU | 1389770 A1 | * | 4/1988 | ............. A61F/2/60 |

* cited by examiner

Primary Examiner—David H. Willse
(74) Attorney, Agent, or Firm—Birch, Stewart, Kolasch & Birch, LLP

(57) ABSTRACT

A drive unit for a prosthetic limb for driving a prosthetic limb with comfort for a long time. A Stirling engine is composed of a displacer unit mounted at an arbitrary portion other than prosthetic limb bodies and a power cylinder unit mounted between the prosthetic limb bodies and for bending/stretching the prosthetic limb bodies and relative to each other. A compression chamber of the displacer unit is connected to an operation chamber of the power cylinder unit via a flexible pressure conduit. A combustor for heating an expansion chamber disposed in a displacer cylinder of the displacer unit is provided around a head portion of the displacer cylinder. A fuel supply device is connected to the combustor. An actuator for arbitrarily driving a displacer piston of the displacer unit is connected to the displacer piston.

18 Claims, 6 Drawing Sheets

DRIVE UNIT FOR PROSTHETIC LIMB

CROSS-REFERENCE TO RELATED APPLICATIONS

The present application claims priority under 35 USC 119 to Japanese Patent Application No. 2001-019120 filed on Jan. 26, 2001 the entire contents thereof is hereby incorporated by reference.

BACKGROUND OF THE INVENTION

1. Field of the Invention

The present invention relates to a drive unit for a prosthetic limb, which unit is adapted to move a prosthetic limb such as a prosthetic arm or a prosthetic leg with a power.

2. Description of Background Art

A hydraulic type drive unit for a prosthetic limb is disclosed in Japanese Patent Publication No. Sho 62-13017. A linear motor type drive unit is disclosed in Japanese Patent Laid-open No. Sho 63-3855. A pneumatic type drive unit is disclosed in Japanese Utility Model Laid-open No. Sho 63-102420.

In the case of adopting a prior art drive unit of any one of the above-described types it is necessary for a battery to be used as a power source for the drive unit. With respect to the use of a battery, since an energy density of the existing battery is as small as about 50 to 100 wh/kg, the battery fails to satisfy the operation of the drive unit for a long time. To cope with such an inconvenience, it may be considered to make use of power generated by an internal combustion engine. However, the use of an internal combustion engine is disadvantageous in terms of exhaust noise, oscillation, etc.

SUMMARY AND OBJECTS OF THE INVENTION

In view of the foregoing, the present invention has been made. It is an object of the present invention is to provide a new drive unit for a prosthetic limb, which is capable of driving a prosthetic limb with comfort for a long time.

To achieve the above object, according to a first feature of the present invention, there is provided a drive unit for a prosthetic limb, adapted to bendably/stretchably drive first and second prosthetic limb bodies, which are connected to each other via a joint, relative to each other. A Stirling engine includes a displacer unit mounted at an arbitrary portion other than the prosthetic limb bodies and a power cylinder unit mounted between the prosthetic limb bodies for bending/stretching the prosthetic limb bodies relative to each other. A compression chamber of the displacer unit is connected to an operation chamber of the power cylinder unit via a flexible pressure conduit. A combustor for heating an expansion chamber disposed in a displacer cylinder of the displacer unit is provided around a head portion of the displacer cylinder. Fuel supply means are operatively connected to the combustor. An actuator is provided for arbitrarily driving a displacer piston of the displacer unit that is connected to the displacer piston. It is to be noted that the first and second prosthetic limb bodies correspond to a thigh portion 2 and a shank portion 4 constituting a prosthetic leg, respectively and the fuel supply means corresponds to a fuel cartridge 38 in an embodiment of the present invention to be described later.

With this first feature, a bending/stretching speed of the second prosthetic limb body relative to the first prosthetic limb body can be controlled from zero to an arbitrary value by controlling an operational speed of the displacer piston from zero to an arbitrary value by means of the actuator. As a result, the prosthetic limb can be moved on the basis of the user's intention.

Since the combustion form in the combustor of the displacer unit is continuous combustion, it is possible to enhance a combustion efficiency and to eliminate any combustion oscillation. In addition, since the fuel supply means is adopted, it is possible to bendably/stretchably drive the prosthetic limb for a long time.

Since only the power cylinder unit is provided on the prosthetic limb bodies and the relatively heavy displacer unit and the fuel supply means are disposed at arbitrary portions other than the first and second prosthetic limb bodies, it is possible to make both the prosthetic limb bodies lightweight and slim while ensuring a smooth bending/stretching motion of both the prosthetic limb bodies.

According to a second feature of the present invention, a hydraulic converter for converting a pressure in the compression chamber into a hydraulic pressure and transmitting the hydraulic pressure to the operation chamber of the power cylinder unit is provided between the compression chamber and the pressure conduit.

With this second feature, since a pressure in the compression chamber of the displacer unit is converted into a hydraulic pressure by the hydraulic converter, and the hydraulic pressure is transferred to the operation chamber of the power cylinder, it is possible to eliminate the occurrence of elastic compression, which has been caused by a working gas, in the pressure conduit and the operation chamber, and hence to improve a pressure transmission efficiency.

According to a third feature of the present invention, power generating means driven by a second Stirling engine is connected to both a storage battery and an electronic control unit for controlling the actuator. It is to be noted that the power generating means corresponds to a power generating coil 73 in the embodiment of the present invention to be described later.

With the third feature, since the power generating means is operated by the second Stirling engine and thereby the storage battery is usually, automatically charged with sufficient electricity, the electronic control unit and the actuator can be normally operated by means of the storage battery. As a result, it is possible to operate the power cylinder unit for a longer time.

According to a fourth feature of the present invention, the displacer unit and the actuator are mounted on a belt worn by a user.

With the fourth feature, a user can easily, rapidly, and simply mount/dismount the displacer unit by mounting/dismounting the belt on a user's body.

According to a fifth feature of the present invention, the first and second prosthetic limb bodies are taken as a thigh portion and a shank portion constituting a prosthetic leg, respectively, and the displacer unit is contained in a hollow portion of a foot portion joined to a lower end of the shank portion.

With the fifth feature, it is possible to dispose the displacer unit by making effective use of a dead space in the foot portion of the prosthetic leg.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The present invention will be described with reference to the accompanying drawings, in which embodiments of the present invention are shown. A first embodiment of the present invention will be first described with reference to FIGS. 1 to 3.

Figure 1:
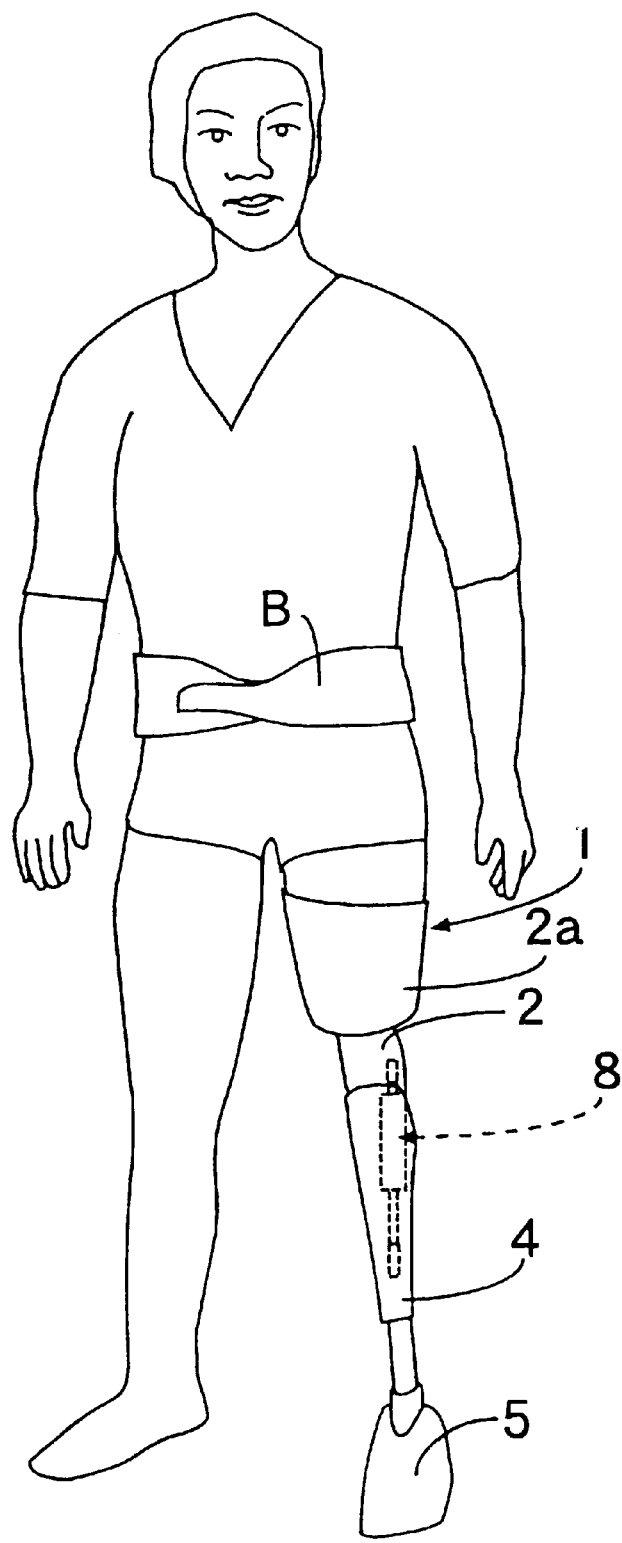
FIG. 1 is a front view of a user wearing a drive unit for a prosthetic limb according to a first embodiment of the present invention.
Figure 2:
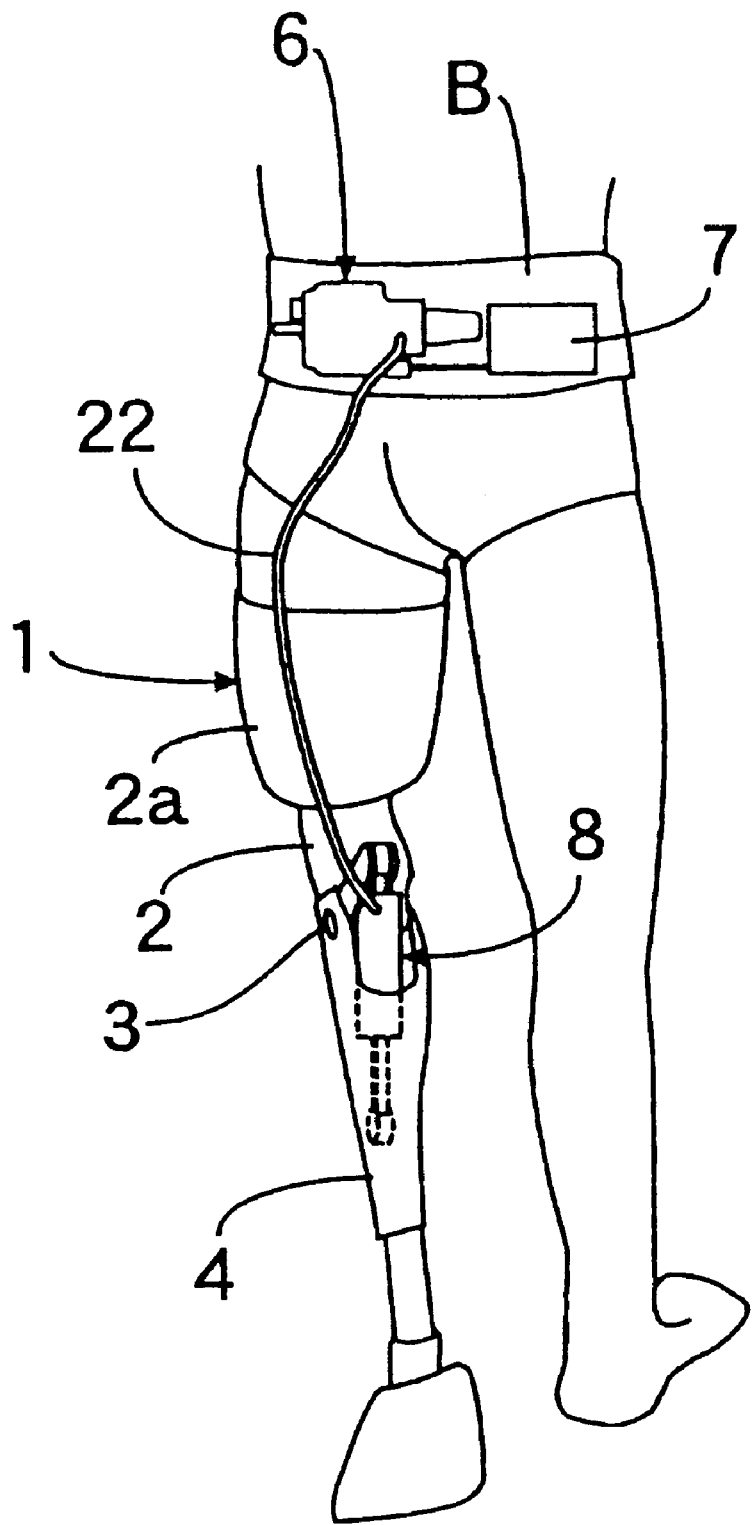
FIG. 2 is a rear view of the user.
Figure 3:
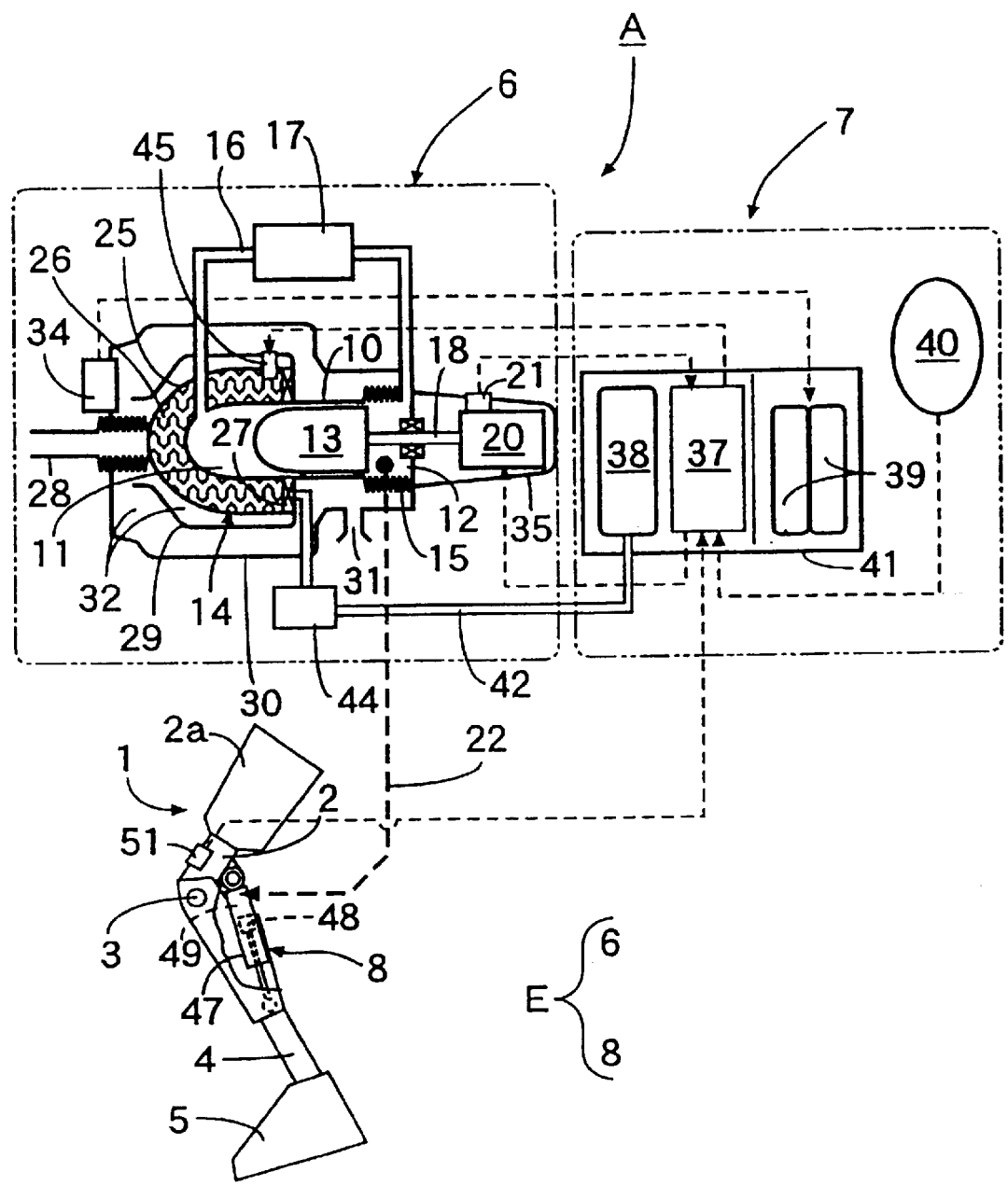
FIG. 3 is a general view of the drive unit for a prosthetic limb, with its essential portion cutaway along the longitudinal direction.

Referring to FIGS. 1 and 2, a prosthetic leg 1 includes a thigh portion 2 integrated with a socket 2a in which a user's remaining thigh portion is to be inserted. A shank portion 4 is bendably/stretchably connected to a lower end of the thigh portion 2 via a joint 3. A foot portion 5 is connected to a lower end of the shank portion 4. A drive unit A for a prosthetic limb of the present invention is used for bending/stretching the shank portion 4 relative to the thigh portion 2. The drive unit A includes a displacer unit 6 and a control unit 7, which are mounted on a belt B worn around a user' waist portion. A power cylinder unit 8 is mounted on the prosthetic leg 1. A pressure conduit 22 is provided for transmitting a pressure generated in the displacer unit 6 to the power cylinder unit 8. A configuration of such a drive unit A for a prosthetic limb will be more fully described with reference to FIG. 3.

The displacer unit 6 includes a displacer cylinder 10 with a displacer piston 13 slidably inserted in the cylinder 10 so as to partition the interior of the cylinder 10 into an expansion chamber 11 on a head side of the cylinder 10 and a compression chamber 12 on a bottom side of the cylinder 10. A combustor 14 is provided on the head portion of the displacer cylinder 10 for heating the expansion chamber 11. A radiator 15 is provided on the bottom portion of the displacer cylinder 10 for cooling the compression chamber 12. A heat regenerator 17 is interposed in a communication port 16 for connecting the expansion chamber 11 to the compression chamber 12. A motor-driven actuator 20 is provided for driving the displacer piston 13 via a rod 18 passing through the bottom portion of the displacer cylinder 10. A displacer piston sensor 21 for detecting a position of the displacer piston 13 is provided on the actuator 20.

The combustor 14 is of a catalyst type in which a combustion housing 25 formed on an outer surface of the head portion of the displacer cylinder 10 is filled with a catalyst 26 for combustion. A fuel-air mixer 27 is provided at one end portion of the combustion housing 25, and an exhaust pipe 28 is provided at the other end of the housing 25.

A heat exchange wall 29 for covering the combustion housing 25 and a base portion of the exhaust pipe 28 is formed around the combustion housing 25. A shroud 30 for covering the heat exchange wall 29 is formed around the heat exchange wall 29. An air intake port 31 formed in the shroud 30 is in communication with an air inlet of the fuel-air mixer 27 via an air passage 32 meandering in each space between two of the combustion housing 25, the heat exchange wall 29, and the shroud 30.

A thermal-electric converting device 34 is additionally provided on the shroud 30 at a position near the heat exchange wall 29. The thermal-electric converting device 34 converts heat transferred from the heat exchange wall 29 into electricity, to charge a storage battery 39 with electricity. A supporting wall 35 for containing the actuator 20 while supporting a fixed portion of the actuator 20 is provided in such a manner as to be continuous to the shroud 30.

The control unit 7 includes an electronic control unit 37, a fuel cartridge 38, the storage battery 39 as a power source for the electronic control unit 37, and a manually operated controller 40 for arbitrarily operating the electronic control unit 37. The electronic control unit 37, the fuel cartridge 38, and the storage battery 39 are contained in a control box 41. The fuel cartridge 38 is filled with a fuel such as benzine, alcohol, or butane.

A fuel outlet of the fuel cartridge 38 is connected to a fuel inlet of the fuel-air mixer 27 via a fuel conduit 42. A fuel adjuster 44 for adjusting a flow rate of fuel is interposed in the fuel conduit 42. An ignition plug 45 is provided in the combustion housing 25 at a position adjacent to the mixer 27.

The power cylinder unit 8 constitutes a Stirling engine E in cooperation with the displacer unit 6. The power cylinder unit 8 includes a power cylinder 47 pivotably connected to one of the thigh portion 2 and the shank portion 4, and a power piston 48 pivotably connected to the other of the thigh portion 2 and the shank portion 4 while slidably inserted in the power cylinder 47. An operation chamber 49 defined in the power cylinder 47 by means of the power piston 48 is in communication with the compression chamber 12 of the displacer unit 6. In this way, the power cylinder unit 8 constitutes the Stirling engine E of a free piston type in cooperation with the displacer unit 6.

A bending/stretching angle sensor 51 for detecting a bending/stretching angle between the thigh portion 2 and the shank portion 4 is mounted at a position between the thigh portion 2 and the shank portion 4. An output signal from the bending/stretching angle sensor 51 outputs signals from the manually operated controller 40 and the displacer piston sensor 21 which are inputted to the electronic control unit 37. On the basis of these signals, the electronic control unit 37 controls the actuator 20 and the fuel adjuster 44.

A function of the first embodiment will be described below.

Fuel is fed from the fuel cartridge 38. The flow rate of the fuel is adjusted by the fuel adjuster 44. The fuel is then supplied to the fuel-air mixer 27, to be mixed with air which flows from the air intake port 31 into the fuel-air mixer 27 via the air passage 32. The fuel-air mixture is ignited once by the ignition plug 45, and thereafter, the combustion of the fuel-air mixture is continuously accelerated by the catalyst 26, to heat the expansion chamber 11 from the head portion side of the displacer cylinder 10 at a specific high temperature. An exhaust gas generated by the combustion is discharged to the outside through the exhaust pipe 28.

The radiator 15 keeps the compression chamber 12 in a specific low temperature state. The heat regenerator 17 receives heat from a working gas which is moving between the expansion chamber 11 and the compression chamber 12 via the communication port 16.

The actuator 20 is operated on the basis of a command from the electronic control unit 37, to reciprocate the displacer piston 13, thereby generating a pressure amplitude in the compression chamber 12. The pressure is transmitted to the operation chamber 49 of the power cylinder 47 via the flexible pressure conduit 22, to reciprocate the power piston 48, thereby bending/stretching the shank portion 4 relative to the thigh portion 2. The bending/stretching motion of the shank portion 2 relative to the thigh portion 4 assists the walking of the user.

At this time, to efficiently drive the power piston 48, the electronic control unit 37 identifies a position of the power piston 48 on the basis of an output signal from the bending/stretching angle sensor 51, and operates the actuator 20 such that the displacer piston 13 is in advance of the power piston 48 by a converted crank angle of 90°. Further, the electronic control units 37 may control the operational speed of the displacer piston 13 from zero to an arbitrary value so as to control the bending/stretching speed of the shank portion 4 relative to the thigh portion 2 from zero to an arbitrary value. With this configuration, the prosthetic leg 1 can be moved on the basis of the user's intention.

As a result of experiments, it was recognized that when a power equivalent to 60 W was generated by using 30 cc of a fuel (liquefied butane) with the aid of the catalyst 26, the drive unit of the present invention could be operated for six hours.

Since the combustion form by the catalyst type combustor 14 is continuous combustion, it is possible to enhance a combustion efficiency and to eliminate any combustion oscillation, and since a fuel cartridge 38 is adopted, it is possible to rapidly supplement fuel and also to operate the drive unit for assisting walking of the user for a long time.

Since power consumption of the storage battery 39 as the power source for the electronic control unit 37 is very small and since part of heat generated by the combustor 14 is converted into electric energy by the thermal-electric converting device 34 to be stored in the storage battery 39, the useful life of the storage battery is increased.

Since only the power cylinder unit 8 is provided on the prosthetic leg 1 while the relatively heavy displacer unit 6, the fuel cartridge 38, the electronic control unit 37, etc. are mounted on the belt B worn around the user's waist portion, and the displacer unit 6 is connected to the power cylinder unit 8 via the pressure conduit 22, it is possible to make the prosthetic leg 1 lightweight and slim while ensuring the smooth bending/stretching motion of the prosthetic leg 1. It is also possible for the user to easily, rapidly, and simply mount/dismount the displacer unit 6 by mounting/dismounting the belt B around the waist portion.

Figure 4:
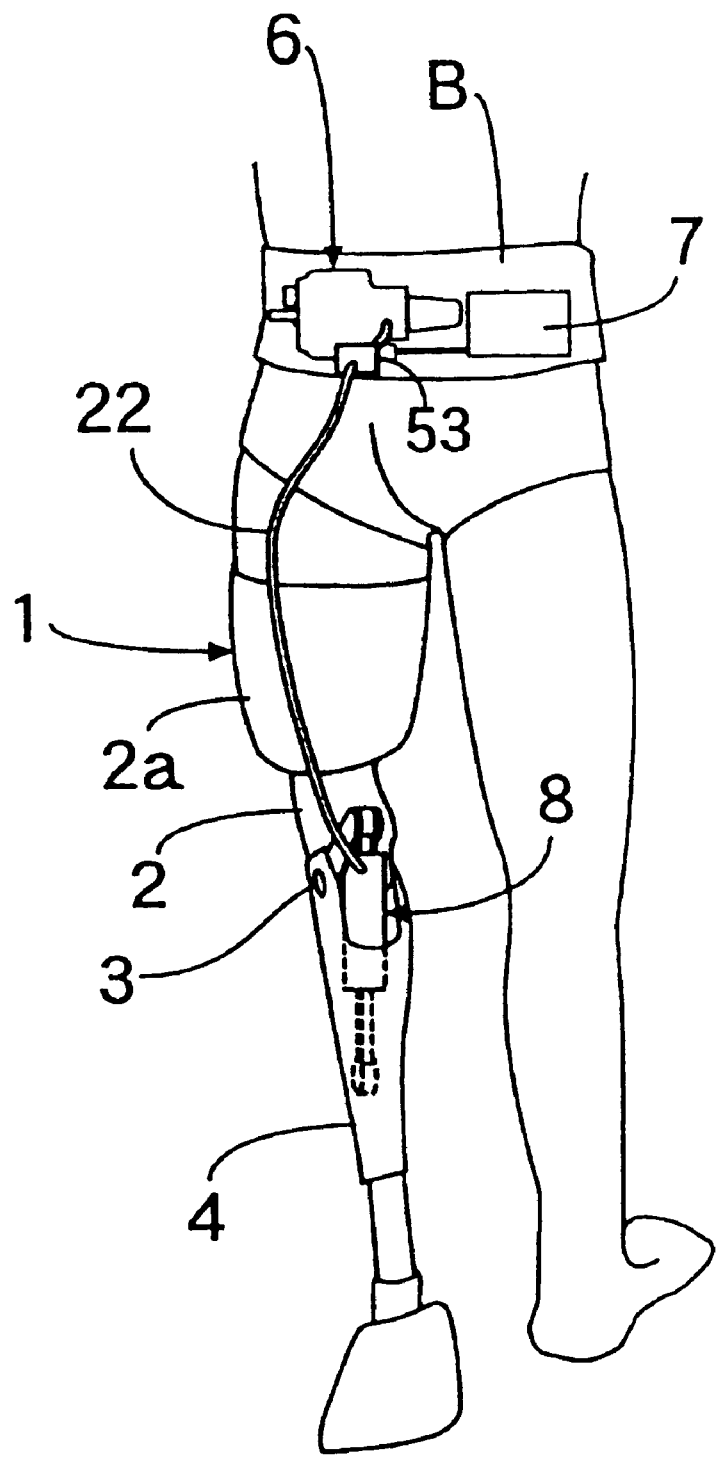
FIG. 4 is a schematic view showing a second embodiment of the present invention.

According to a second embodiment of the present invention shown in FIG. 4, a hydraulic converter 53 for converting the pressure in the compression chamber 12 into a hydraulic pressure is provided on the displacer unit 6, and an output port of the hydraulic converter 53 is connected to the operation chamber 49 of the power cylinder 47 via the pressure conduit 22. The other configurations are the same as those of the first embodiment, and therefore, parts in FIG. 4 corresponding to those in the first embodiment are designated by the same reference numerals and the overlapped description thereof is omitted.

According to the second embodiment, since the pressure in the compression chamber 12 of the displacer unit 6 is converted into a hydraulic pressure by the hydraulic converter 53, and the hydraulic pressure is transferred to the operation chamber 49 of the power cylinder 47, it is possible to eliminate occurrence of elastic compression, which has been caused for a working gas, in the pressure conduit 22 and the operation chamber 49, and hence to improve a pressure transmission efficiency.

Figure 5:
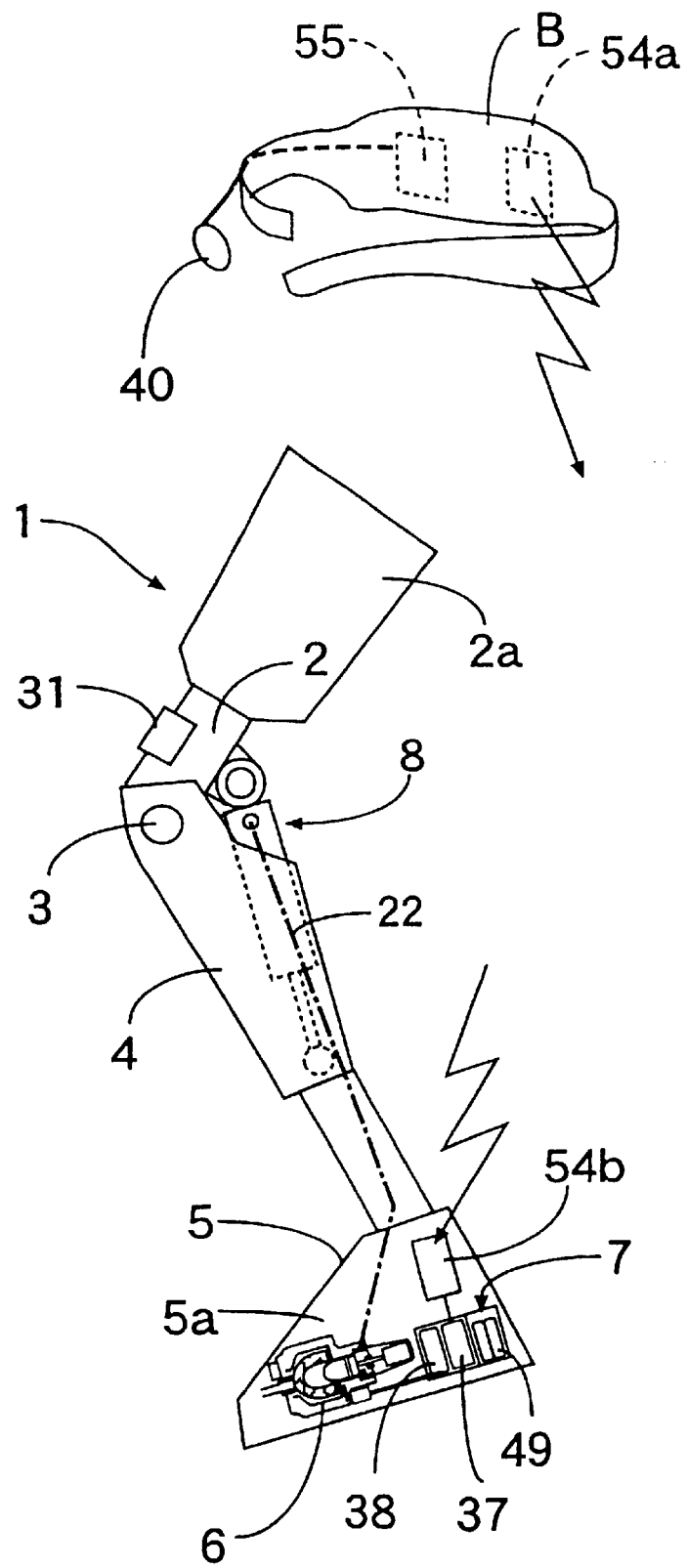
FIG. 5 is a schematic view showing a third embodiment of the present invention.

According to a third embodiment of the present invention shown in FIG. 5, the displacer unit 6, the fuel cartridge 38, the electronic control unit 37, and the storage battery 39, and further a communication unit 54b connected to the electronic control unit 37 are contained in a hollow portion 5a of the foot portion 5 of the prosthetic leg 1, while the manually operated controller 40, a general control unit 55 for processing an output signal from the manually operated controller 40, and a communication unit 54a for generating a radio wave corresponding to an output signal from the general control unit 55 are mounted to the belt B. The power cylinder unit 8 is operated by a radio wave transferred between both the communications 54a and 54b. The other configurations are the same as those of the second embodiment, and therefore, parts in FIG. 5 corresponding to those in the second embodiment are designated by the same reference numerals and the overlapped description thereof is omitted.

According to the third embodiment, it is possible to dispose the displacer unit 6, etc. by making effective use of a dead space in the foot portion 5 of the prosthetic leg 1.

A fourth embodiment of the present invention will be described with reference to FIG. 6.

A first displacer unit 6 and a second displacer unit 60 are mounted on the belt B. The first displacer unit 6 has the same configuration as that of the displacer unit 6 in the first embodiment, and a compression chamber 12 thereof is connected to an operation chamber 49 of a power cylinder unit 8 of a prosthetic leg 1 via a pressure conduit 22.

A permanent magnet 63 is additionally provided in a displacer piston 62 inserted in a displacer cylinder 61 of the second displacer unit 60, and a drive coil 64 for driving the displacer piston 62 in cooperation with the permanent magnet 63 is fixedly provided on a bottom portion of the displacer cylinder 61. A power cylinder 65 is provided on a bottom portion of the displacer cylinder 61 in such a manner as to be coaxial with the displacer cylinder 61. A power piston 66 having a permanent magnet 72 is slidably inserted in the power cylinder 65. The interior of the power cylinder 65 is partitioned into an operation chamber 67 on a head side and a spring chamber 68 on a bottom side by means of the power piston 66. The operation chamber 67 is communicated to a compression chamber 77 of the displacer cylinder 61. A spring 69 for biasing the power piston 66 to the operation chamber 67 side is contained in the spring chamber 68.

A combustor 14, commonly used for the first displacer unit 6 and the second displacer unit 60, is provided on a head side of the displacer cylinder 61, and a radiator 80 is additionally provided on a bottom portion of the displacer cylinder 61. A heat regenerator 79 is interposed in a communication port 78 for communicating an expansion chamber 76 to a compression chamber 77.

A power generating coil 73 for generating power in cooperation with a permanent magnet 72 is additionally provided around the power piston 66 around an outer periphery of the power cylinder 65. A displacer drive circuit 75 is inserted in an electric circuit 74 for connecting the power generating coil 73 to the drive coil 64. The electric circuit 74 is also connected to a storage battery 39. The power cylinder 65 and the power piston 66 constitute a second Stirling engine E' in cooperation with the second displacer unit 66.

Figure 6:
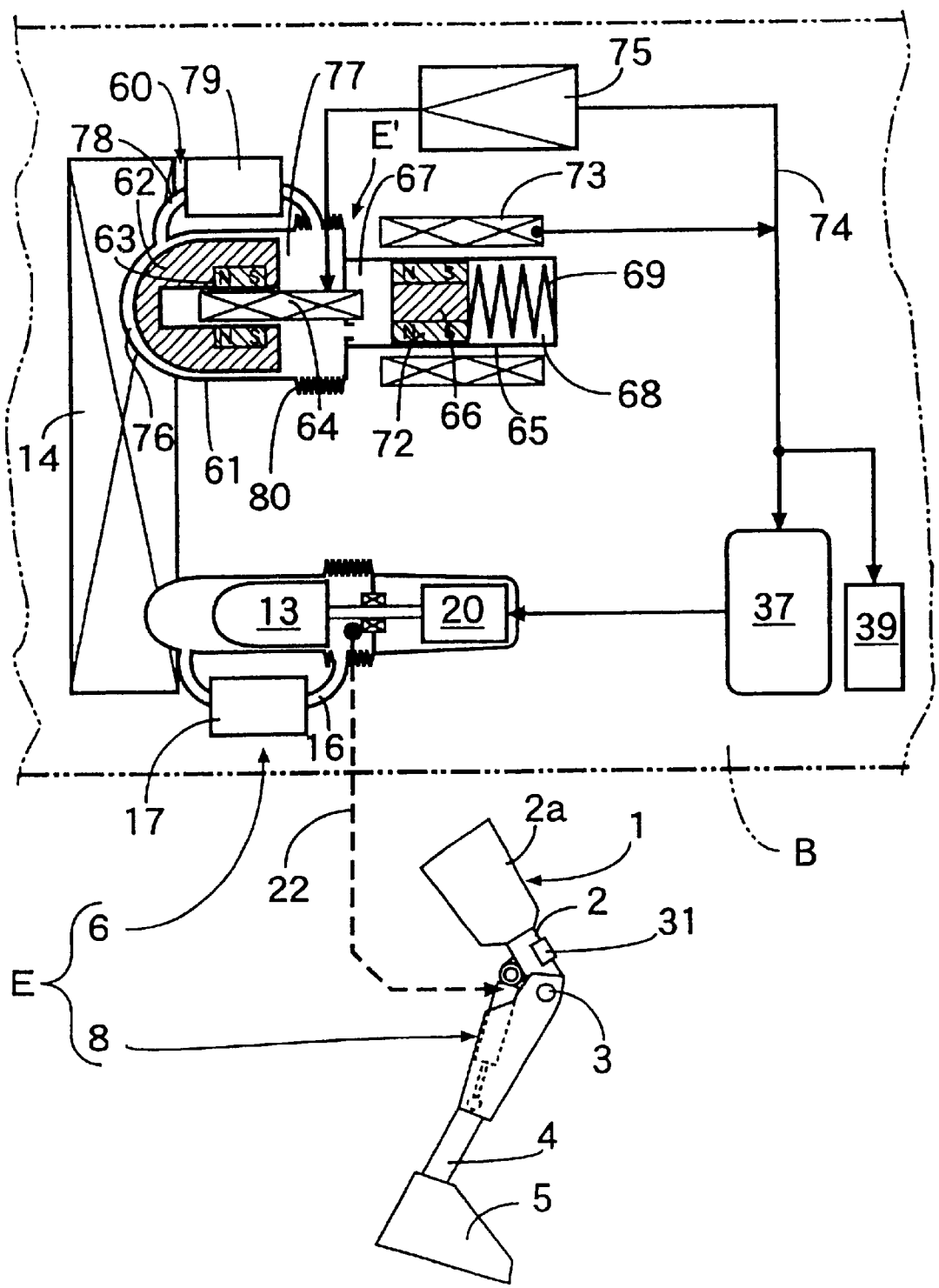
FIG. 6 is a schematic view showing a fourth embodiment of the present invention.

The other configurations are the same as those of the first embodiment, and therefore, parts in FIG. 6 corresponding to those in the first embodiment are designated by the same reference numerals and the overlapped description thereof is omitted.

According to the fourth embodiment, after the displacer piston 62 is once reciprocated by driving the drive coil 64 via the displacer drive circuit 75, a pressure amplitude generated in the compression chamber 77 is transferred to the operation chamber 67 of the power cylinder 65, to freely oscillate the power piston 66 having the permanent magnet 72 in cooperation with the spring 69, so that electric energy is taken out of the power generating coil 73 and is supplied to the storage battery 39 and the electronic control unit 37.

With this configuration, since the storage battery 39 is usually, automatically charged with sufficient electricity, it can usually, certainly operate the actuator 20 of the first displacer unit 6. As a result, it is possible to operate the power cylinder unit 8 of the drive unit for assisting the walking of the user for a longer time.

The present invention is not limited to the above-described embodiments, and it is to be understood that various changes in design may be made without departing from the scope of the present invention. For example, the present invention can be applied to drive a prosthetic arm. The present invention can also be modified such that the first and second prosthetic limb bodies are mounted to a leg or an arm of a normal worker for giving care to patients or performing heavy work, and are driven by the drive unit A of the present invention, to thereby reduce labor for the worker.

As described above, according to the first feature of the present invention, there is provided a drive unit for a prosthetic limb, adapted to bendably/stretchably drive first and second prosthetic limb bodies, which are connected to each other via a joint, relative to each other. A Stirling engine is composed of a displacer unit mounted at an arbitrary portion other than the prosthetic limb bodies and a power cylinder unit mounted between the prosthetic limb bodies for bending/stretching the prosthetic limb bodies relative to each other. A compression chamber of the displacer unit is connected to an operation chamber of the power cylinder unit via a flexible pressure conduit. A combustor for heating an expansion chamber is disposed in a displacer cylinder of the displacer unit and is provided around a head portion of the displacer. Fuel supply means are connected to the combustor. An actuator is provided for arbitrarily driving a displacer piston of the displacer unit and is connected to the displacer piston. Accordingly, a bending/stretching speed of the second prosthetic limb body relative to the first prosthetic limb body can be controlled from zero to an arbitrary value by controlling an operational speed of the displacer piston from zero to an arbitrary value by means of the actuator. As a result, the prosthetic limb can be moved on the basis of the user's intention. Also, since the combustion form in the combustor of the displacer unit is continuous combustion, it is possible to enhance a combustion efficiency and to eliminate any combustion oscillation. In addition, since a fuel supply means is adopted, it is possible to bendably/stretchably drive the prosthetic limb for a long time. Further, since only the power cylinder unit is provided on the prosthetic limb bodies and the relatively heavy displacer unit and the fuel supply means are disposed at arbitrary portions other than the first and second prosthetic limb bodies, it is possible to make both the prosthetic limb bodies lightweight and slim while ensuring a smooth bending/stretching motion of both the prosthetic limb bodies.

According to the second feature of the present invention, a hydraulic converter for converting a pressure in the compression chamber into a hydraulic pressure and transmitting the hydraulic pressure to the operation chamber of the power cylinder unit is provided between the compression chamber and the pressure conduit. Accordingly, it is possible to eliminate the occurrence of elastic compression, which has been caused for a working gas, in the pressure conduit and the operation chamber, and hence to improve a pressure transmission efficiency.

According to the third feature of the present invention, power generating means driven by a second Stirling engine is connected to both a storage battery and an electronic control unit for controlling the actuator. Accordingly, since the storage battery is normally charged with sufficient electricity by the power generating means operated by the second Stirling engine, the electronic control unit and the actuator can be usually, certainly operated by means of the storage battery. As a result, it is possible to operate the power cylinder unit for a longer time.

According to the fourth feature of the present invention, the displacer unit and the actuator are mounted on a belt worn by a user. Accordingly, a user can easily, rapidly, and simply mount/dismount the displacer unit by mounting/dismounting the belt on a user's body.

According to the fifth feature of the present invention, the first and second prosthetic limb bodies are taken as a thigh portion and a shank portion constituting a prosthetic leg, respectively, and the displacer unit is contained in a hollow portion of a foot portion joined to a lower end of the shank portion. Accordingly, it is possible to dispose the displacer unit by making effective use of a dead space in the foot portion of the prosthetic leg.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A drive unit for a prosthetic limb, adapted to bendably and/or stretchably drive first and second prosthetic limb bodies, which are connected to each other via a joint, relative to each other comprising:

a Stirling engine including a displacer unit which is not mounted on said prosthetic limb bodies and a power cylinder unit mounted between said prosthetic limb bodies for bending and/or stretching said prosthetic limb bodies relative to each other;

a compression chamber of said displacer unit operatively connected to an operation chamber of said power cylinder unit via a flexible pressure conduit;

a combustor for heating an expansion chamber disposed in a displacer cylinder of said displacer unit, said combustor being provided around a head portion of said displacer cylinder;

fuel supply means operatively connected to said combustor; and an actuator for selectively driving a displacer piston of said displacer unit, said actuator being connected to said displacer piston.

2. The drive unit for a prosthetic limb according to claim 1, wherein a hydraulic converter converts pressure in said compression chamber into a hydraulic pressure and transmits the hydraulic pressure to said operation chamber of said power cylinder unit, said hydraulic converter is provided between said compression chamber and said pressure conduit.

3. The drive unit for a prosthetic limb according to claim 1, wherein power generating means driven by a second Stirling engine is connected to both a storage battery and an electronic control unit for controlling said actuator.

4. The drive unit for a prosthetic limb according to a claim 1, wherein said displacer unit and said actuator are mounted on a belt worn by a user.

5. The drive unit for a prosthetic limb according to a claim 2, wherein said displacer unit and said actuator are mounted on a belt worn by a user.

6. The drive unit for a prosthetic limb according to a claim 3, wherein said displacer unit and said actuator are mounted on a belt worn by a user.

7. The drive unit for a prosthetic limb according to claim 1, wherein said first and second prosthetic limb bodies are a thigh portion and a shank portion constituting a prosthetic leg, respectively, and said displacer unit is contained in a hollow portion of a foot portion joined to a lower end of said shank portion.

8. The drive unit for a prosthetic limb according to claim 2, wherein said first and second prosthetic limb bodies are a thigh portion and a shank portion constituting a prosthetic leg, respectively, and said displacer unit is contained in a hollow portion of a foot portion joined to a lower end of said shank portion.

9. The drive unit for a prosthetic limb according to claim 3, wherein said first and second prosthetic limb bodies are a thigh portion and a shank portion constituting a prosthetic leg, respectively, and said displacer unit is contained in a hollow portion of a foot portion joined to a lower end of said shank portion.

10. A drive unit for a prosthetic limb, adapted to bendably and/or stretchably drive first and second prosthetic limb bodies, which are connected to each other via a joint, relative to each other comprising:

a Stirling engine comprising:
  a displacer unit not mounted on the prosthetic limb bodies;
  a power cylinder unit mounted between said prosthetic limb bodies for bending and/or stretching said prosthetic limb bodies relative to each other;
  said displacer unit including a compression chamber operatively connected to an operation chamber of said power cylinder unit via a flexible pressure conduit;
  an expansion chamber disposed in a displacer cylinder of said displacer unit, said expansion chamber being provided around a head portion of said displacer cylinder;
  a combustor for heating said expansion chamber; and
  an actuator for selectively driving a displacer piston of said displacer unit, said actuator being connected to said displacer piston.

11. The drive unit for a prosthetic limb according to claim 10, wherein a hydraulic converter converts pressure in said compression chamber into a hydraulic pressure and transmits the hydraulic pressure to said operation chamber of said power cylinder unit, said hydraulic converter being provided between said compression chamber and said pressure conduit.

12. The drive unit for a prosthetic limb according to claim 10, wherein power generating means driven by a second Stirling engine is connected to both a storage battery and an electronic control unit for controlling said actuator.

13. The drive unit for a prosthetic limb according to a claim 10, wherein said displacer unit and said actuator are mounted on a belt worn by a user.

14. The drive unit for a prosthetic limb according to a claim 11, wherein said displacer unit and said actuator are mounted on a belt worn by a user.

15. The drive unit for a prosthetic limb according to a claim 12, wherein said displacer unit and said actuator are mounted on a belt worn by a user.

16. The drive unit for a prosthetic limb according to claim 10, wherein said first and second prosthetic limb bodies are a thigh portion and a shank portion constituting a prosthetic leg, respectively, and said displacer unit is contained in a hollow portion of a foot portion joined to a lower end of said shank portion.

17. The drive unit for a prosthetic limb according to claim 11, wherein said first and second prosthetic limb bodies are a thigh portion and a shank portion constituting a prosthetic leg, respectively, and said displacer unit is contained in a hollow portion of a foot portion joined to a lower end of said shank portion.

18. The drive unit for a prosthetic limb according to claim 12, wherein said first and second prosthetic limb bodies are a thigh portion and a shank portion constituting a prosthetic leg, respectively, and said displacer unit is contained in a hollow portion of a foot portion joined to a lower end of said shank portion.

* * * * *